(12) United States Patent
Gu et al.

(10) Patent No.: US 9,891,999 B2
(45) Date of Patent: Feb. 13, 2018

(54) EXERCISE HISTORY INFORMATION MANAGING METHOD AND ELECTRONIC DEVICE SUPPORTING THE SAME

(71) Applicant: Samsung Electronics Co., Ltd., Gyeonggi-do (KR)

(72) Inventors: Heum Mo Gu, Gyeonggi-do (KR); Ji Young Kong, Gyeonggi-do (KR); Srivastava Sonika, Bangalore (IN); Kyung Sub Min, Gyeonggi-do (KR); Ik Hwan Cho, Gyeonggi-do (KR); Seung Wok Han, Seoul (KR)

(73) Assignee: Samsung Electronics Co. Ltd. (KR)

( * ) Notice: Subject to any disclaimer, the term of this patent is extended or adjusted under 35 U.S.C. 154(b) by 74 days.

(21) Appl. No.: 14/989,538

(22) Filed: Jan. 6, 2016

(65) Prior Publication Data

US 2016/0196185 A1    Jul. 7, 2016

(30) Foreign Application Priority Data

Jan. 6, 2015  (KR) .................. 10-2015-0001289

(51) Int. Cl.
*G06F 11/00*    (2006.01)
*G06F 11/14*    (2006.01)
(Continued)

(52) U.S. Cl.
CPC ........ *G06F 11/1435* (2013.01); *A61B 5/1118* (2013.01); *G06F 11/1438* (2013.01); *G06F 11/30* (2013.01); *G06F 11/3065* (2013.01); *G09B 5/02* (2013.01); *G09B 19/0038* (2013.01); *G06F 2201/805* (2013.01)

(58) Field of Classification Search
CPC ............... G06F 11/305; G06F 11/3065; G06F 11/1471; G06F 11/30
See application file for complete search history.

(56) References Cited

U.S. PATENT DOCUMENTS 6,067,550 A * 5/2000 Lomet ................. G06F 11/1471
6,782,350 B1 * 8/2004 Burnley .............. G06F 11/3419
                                                        702/177
(Continued)

FOREIGN PATENT DOCUMENTS

WO   WO 2010/126821    11/2010
WO   WO 2012/083177    6/2012

OTHER PUBLICATIONS

Shane Conder et al., "Android Barometer Logger: Acquiring Sensor Data", XP055270928, Apr. 30, 2012, 14 pages.
(Continued)

*Primary Examiner* — Charles Ehne
(74) *Attorney, Agent, or Firm* — The Farrell Law Firm, P.C.

(57) ABSTRACT

An electronic device is provided. The electronic device includes a processor configured to record exercise history information relating to an exercise performed by a user of the electronic device, and a memory configured to store the exercise history information, wherein the processor is configured to record the exercise history information continuously if an exercise application of the electronic device is unintentionally terminated, and retrieve the stored exercise history information when the exercise application is restarted.

18 Claims, 7 Drawing Sheets

(51) Int. Cl.
*G06F 11/30* (2006.01)
*A61B 5/11* (2006.01)
*G09B 19/00* (2006.01)
*G09B 5/02* (2006.01)

(56) References Cited

U.S. PATENT DOCUMENTS

| | | | |
|---|---|---|---|
| 8,001,472 | B2 | 8/2011 | Gilley et al. |
| 8,562,489 | B2 | 10/2013 | Burton et al. |
| 8,597,093 | B2 | 12/2013 | Engelberg et al. |
| 9,122,250 | B2 | 9/2015 | Hoffman et al. |
| 9,329,053 | B2 | 5/2016 | Lakovic et al. |
| 2007/0277172 | A1* | 11/2007 | Kawakami ......... H04N 7/17318 718/100 |
| 2008/0077620 | A1 | 3/2008 | Gilley et al. |
| 2008/0228833 | A1* | 9/2008 | Kano .................. G06F 11/1469 |
| 2008/0234890 | A1* | 9/2008 | Okada ................ B60R 21/0132 701/33.4 |
| 2008/0307220 | A1* | 12/2008 | Campbell .............. G06Q 20/02 713/155 |
| 2010/0331145 | A1 | 12/2010 | Lakovic et al. |
| 2011/0003665 | A1 | 1/2011 | Burton et al. |
| 2011/0007468 | A1 | 1/2011 | Burton et al. |
| 2011/0032105 | A1 | 2/2011 | Hoffman et al. |
| 2011/0281687 | A1 | 11/2011 | Gilley et al. |
| 2012/0290109 | A1 | 11/2012 | Engelberg et al. |
| 2013/0123068 | A1* | 5/2013 | Sultan ................ A63B 24/0062 482/2 |
| 2014/0149784 | A1* | 5/2014 | Ngo .................... H04L 67/1008 714/4.11 |
| 2015/0169663 | A1 | 6/2015 | Sultan et al. |
| 2015/0338236 | A1 | 11/2015 | Hoffman et al. |
| 2017/0216668 | A1 | 8/2017 | Burton et al. |
| 2017/0261335 | A1 | 9/2017 | Hoffman et al. |

OTHER PUBLICATIONS

Anonymous: "A Background Sensor Data Collector in Anroid—Stack Overflow", XP055270859, Mar. 1, 2014, 2 pages.
Anonymous: "Failover—Wikipedia, the free Encyclopedia", XP055269923, Jun. 25, 2014, 2 pages.
European Search Report dated May 18, 2016 issued in counterpart application No. 15202833.8-1958, 8 pages.
European Office Action dated Mar. 24, 2017 issued in counterpart application No. 15202833.8-1958, 6 pages.
European Search Report dated Nov. 29, 2017 issued in counterpart applicaton No. 15202833.8-1958, 7 pages.

* cited by examiner

EXERCISE HISTORY INFORMATION MANAGING METHOD AND ELECTRONIC DEVICE SUPPORTING THE SAME

PRIORITY

This application claims priority under 35 U.S.C. § 119(a) to Korean Patent Application Serial No. 10-2015-0001289, which was filed in the Korean Intellectual Property Office on Jan. 6, 2015, the entire disclosure of which is incorporated herein by reference.

BACKGROUND

1. Field of the Disclosure

The present disclosure relates generally to method for managing exercise history information, and more particularly, to a method for managing and securing exercise history information of a user when an exercise service including an exercise application is unintentionally terminated.

2. Description of the Related Art

Recently, there has been a growing interest in exercising to maintain good health. Accordingly, electronic devices provide exercise services which help a user to manage a more systematic and planned way to exercise. For examples, electronic devices have been configured to provide exercise services including exercise applications that are set to recommend proper exercises to a user and to display his/her exercise history information.

However, in the case where recording a user's exercise history information is unintentionally terminated, e.g., due to a dead battery of an electronic device, a user's negligence, or the like, during an exercise, the above-mentioned exercise service may not provide proper information due to the loss of the exercise history information.

SUMMARY

The present disclosure has been made to address at least the above-mentioned problems and/or disadvantages and to provide at least the advantages described below.

Accordingly, an aspect of the present disclosure provides an exercise history information managing method which secures exercise history information of a user when there is an unintentional termination of an exercise service including an exercise application, and an electronic device supporting the same.

In accordance with an aspect of the present disclosure there is provided an electronic device. The electronic device includes a processor that is configured to record exercise history information relating to an exercise performed by a user of the electronic device, and a memory configured to store the exercise history information, wherein the processor is configured to record the exercise history information continuously if an exercise application of the electronic device is unintentionally terminated, and retrieve the stored exercise history information when the exercise application is restarted.

In accordance with an aspect of the present disclosure there is provided a method for managing exercise history information in an electronic device. The method includes recording exercise history information relating to an exercise performed by a user of the electronic device continuously if an exercise application of the electronic device is unintentionally terminated, storing the exercise history information, and retrieving the stored exercise history information when the exercise application is restarted.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
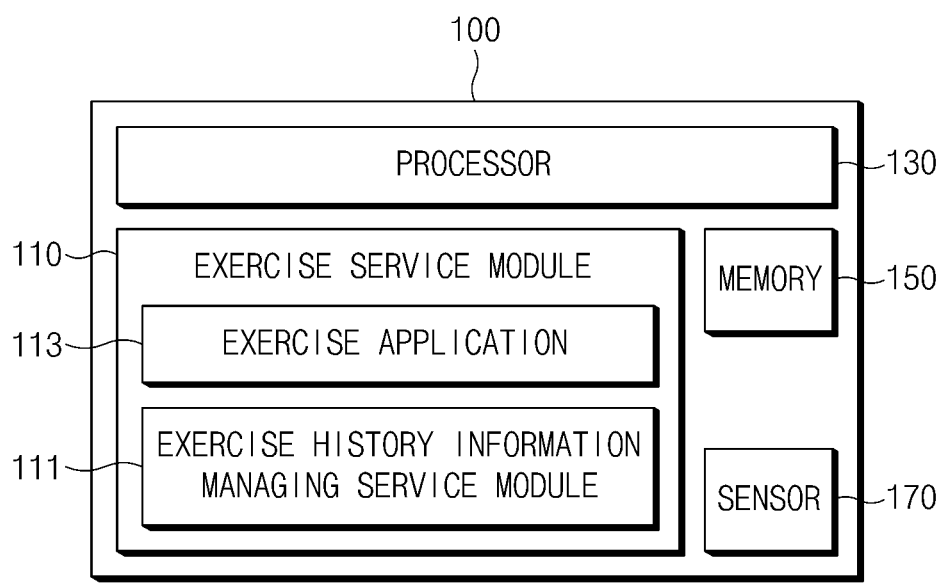
FIG. 1 is a diagram illustrating an electronic device for providing an exercise service, according to an embodiment of the present disclosure.

Embodiments of the present disclosure will be described herein below with reference to the accompanying drawings. However, the embodiments of the present disclosure are not limited to the specific embodiments and should be construed as including all modifications, changes, equivalent devices and methods, and/or alternative embodiments of the present disclosure. In the description of the drawings, similar reference numerals are used for similar elements.

The terms "have," "may have," "include," and "may include" as used herein indicate the presence of corresponding features (for example, elements such as numerical values, functions, operations, or parts), and do not preclude the presence of additional features.

The terms "A or B," "at least one of A or/and B," or "one or more of A or/and B" as used herein include all possible combinations of items enumerated with them. For example, "A or B," "at least one of A and B," or "at least one of A or B" means (1) including at least one A, (2) including at least one B, or (3) including both at least one A and at least one B.

The terms such as "first" and "second" as used herein may modify various elements regardless of an order and/or importance of the corresponding elements, and do not limit the corresponding elements. These terms may be used for the purpose of distinguishing one element from another element. For example, a first user device and a second user device may indicate different user devices regardless of the order or importance. For example, a first element may be referred to as a second element without departing from the scope the present invention, and similarly, a second element may be referred to as a first element.

The term "module" as used herein may represent, for example, a unit including one or more combinations of hardware, software and firmware. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" may include at least one of an application-specific IC (ASIC) chip, a field-programmable gate array (FPGA), and a programmable-logic device for performing some operations, which are known or will be developed.

It will be understood that, when an element (for example, a first element) is "(operatively or communicatively) coupled with/to" or "connected to" another element (for example, a second element), the element may be directly coupled with/to another element, and there may be an intervening element (for example, a third element) between the element and another element. To the contrary, it will be understood that, when an element (for example, a first element) is "directly coupled with/to" or "directly connected to" another element (for example, a second element), there is no intervening element (for example, a third element) between the element and another element.

The expression "configured to (or set to)" as used herein may be replaced with "suitable for," "having the capacity to," "designed to," "adapted to," "made to," or "capable of" according to a context. The term "configured to (set to)" does not necessarily mean "specifically designed to" in a hardware level. Instead, the expression "apparatus configured to . . . " may mean that the apparatus is "capable of . . . " along with other devices or parts in a certain context. For example, "a processor configured to (set to) perform A, B, and C" may mean a dedicated processor (e.g., an embedded processor) for performing a corresponding operation, or a generic-purpose processor (e.g., a CPU or an application processor) capable of performing a corresponding operation by executing one or more software programs stored in a memory device.

The terms used in describing the various embodiments of the present disclosure are just for the purpose of describing particular embodiments and are not intended to limit the present disclosure. As used herein, the singular forms are intended to include the plural forms as well, unless the context clearly indicates otherwise. All of the terms used herein including technical or scientific terms have the same meanings as those generally understood by an ordinary skilled person in the related art unless they are defined otherwise. The terms defined in a generally used dictionary should be interpreted as having the same or similar meanings as the contextual meanings of the relevant technology and should not be interpreted as having ideal or exaggerated meanings unless they are clearly defined herein. According to circumstances, even the terms defined in this disclosure should not be interpreted as excluding the embodiments of the present disclosure.

Hereinafter, electronic devices will be described with reference to the accompanying drawings. The term "user" as used herein may refer to a person who uses an electronic device or may refer to a device (e.g., an artificial intelligence electronic device) that uses an electronic device.

FIG. 1 is a diagram illustrating an electronic device 100 for providing an exercise service, according to an embodiment of the present disclosure.

Referring to FIG. 1, the electronic device 100 may include an exercise service module 110, a processor 130, a memory 150, and a sensor 170.

The exercise service module 110 may provide an exercise service to a user. For example, the exercise service module 110 may manage an exercise history of the user so that the user can perform a systematic and planned exercise. The exercise service module 1110 may recommend an appropriate exercise based on the exercise history and body information of the user. Furthermore, the exercise service module 110 may display exercise history information about an exercise performed by the user. To perform the above-mentioned functions, the exercise service module 110 may include an exercise history information managing service module 111 (or more simply exercise module 111) and an exercise application 113. The exercise service module 110 may include one of hardware, software, or firmware or a combination of two or more thereof.

The exercise history information managing service module 111 may manage the exercise history information relating to an exercise performed by the user. For example, the exercise history information managing service module 111 may manage an exercise time, exercise information, real-time exercise data, an exercise progress rate, or the like. According to an embodiment of the present disclosure, the exercise history information managing service module 111 may store the above-mentioned exercise history information in the memory 150. Furthermore, the exercise history information managing service module 111 may deliver the exercise history information to the exercise application 113.

The exercise history information managing service module 111 may analyze sensor information about the exercise collected from the sensor 170 and may produce exercise data. Furthermore, the exercise history information managing service module 111 may determine the exercise progress rate using the exercise time and the exercise data.

The exercise history information managing service module 111 may operate in conjunction with the exercise application 113. For example, the exercise history information managing service module 111 may receive an exercise time, exercise information, an exercise goal, or the like about a specific exercise through the exercise application 113. The exercise history information managing service module 111 may deliver produced real-time exercise data, exercise progress rate, or the like to the exercise application 113. According to an embodiment of the present disclosure, after the specific exercise is completed, the exercise history information managing service module 111 may set and save completion indicating information together with the exercise history information of the exercise performed by a user through the exercise application 113.

The exercise history information managing service module 111 may record the exercise history information independently of the exercise application 113. For example, if/when the exercise application 113 is abnormally or unintentionally terminated, the exercise history information managing service module 111 may continuously record the exercise history information. Furthermore, the exercise history information managing service module 111 may perform a notification function informing that the exercise application 113 has been unintentionally terminated. For example, the exercise history information managing service module 111 may perform control to output at least one of a user interface including an object on a display of the electronic device 100 or voice (or audio) information based on an exercise status and whether the exercise application 113 has been unintentionally terminated.

The exercise history information managing service module 111 may monitor a status of the electronic device 100 while an exercise is being performed by a user of the electronic device 100 in real time. According to an embodiment of the present disclosure, the exercise history information managing service module 111 may monitor a state of charge, a memory usage, a remaining capacity, and the like of the electronic device 100 while the user is performing exercise. For example, the exercise history information managing service module 111 may receive an event related to the state of charge from a power management module included in the electronic device 100 while the user is performing exercise. Furthermore, the exercise history information managing service module 111 may provide the user with the state of charge, a minimum of available exercise time according to the state of charge, and the like in response to the event.

According to an embodiment of the present disclosure, the exercise history information managing service module 111 may perform control to output the voice information corresponding to the state of charge, the minimum of available exercise time, and the like in response to an event which occurs at a low-battery status while the user is performing the exercise. Furthermore, the exercise history information managing service module 111 may monitor the usage and remaining capacity of the memory 150 while the user is performing the exercise. For example, the exercise history information managing service module 111 may calculate a remaining capacity of the memory 150 and an expected usage of the memory 150 based on the exercise history information and may notify the user of an available space of the memory 150 with the voice information, such as in a case where the available space of the memory 150 is insufficient.

The exercise application 113 may be an application program which is set to provide the user with exercise services, such as, for example, management of the exercise history of the user, recommending an appropriate exercise to the user, displaying the exercise history information relating to the exercise performed by the user, or the like. According to an embodiment of the present disclosure, the exercise application 113 may be set or configured to collect a user's body information, for example, an age, a gender, a height, a weight, and the like and to recommend the appropriate exercise to the user. The exercise application 113 may provide the exercise history information managing service module 111 with information such as a kind of exercise, a frequency of the exercise, an intensity of the exercise, a difficulty of the exercise, a time duration of the exercise, or other information relating to an exercise performed by the user and may store the information in the memory 150. Furthermore, the exercise application 113 may perform control to display the exercise history information using the display of the electronic device 100. For example, the exercise application 113 may display an object such as a map, a chart, or the like on the display of the electronic device 100, or the exercise application 113 may perform control to output the exercise history information using the voice information.

The processor 130 may perform an arithmetic operation or data processing associated with control and/or communication of at least one other component(s) included in the electronic device 100. The processor 130 may control the exercise history information managing service module 111 and the exercise application 113 included in the exercise service module 110 related to the exercise service. For example, the processor 130 may run the exercise history information managing service module 111 and the exercise application 113 stored in the memory 150 in a program module form. For example, the processor 130 may load instructions, which are defined to perform functions of the exercise history information managing service module 111 and the exercise application 113, from the memory 150 and may execute the corresponding instructions according to a program routine.

According to various embodiments of the present disclosure, the processor 130 may assign a unique identifier (ID) in response to an execution of at least one application or module, such as the managing service module 111. According to an embodiment of the present disclosure, the processor 130 may control a life cycle of the corresponding module based on the ID. For example, in the case where the exercise history information managing service module 111 is unintentionally terminated and is then newly executed, i.e., restarted, the processor 130 may delete a previously assigned ID and may assign a new ID. The processor 130 may determine whether the module is running or terminated, in the above-mentioned manner.

According to various embodiments of the present disclosure, with regard to the unintentional termination of the exercise service provided by the exercise service module 111, the processor 130 may determine whether the exercise application 113 and the exercise history information managing service module 111 are terminated. The processor 130 may set a method, which provides a continuity of the corresponding exercise history information, in different ways based on whether one of the above-mentioned components of the exercise service module 111 is terminated. For example, the processor 130 may continuously perform control to record the exercise history information through the exercise history information managing service module 111 in the case where only the exercise application 113 is unintentionally terminated. Furthermore, the processor 130 may provide the continuity of the exercise history information by configuring a screen based on the exercise history information at a point in time when the exercise application 113 is unintentionally terminated and is then restarted. According to an embodiment of the present disclosure, in the case where both the exercise history information managing service module 111 and the exercise application 113 are unintentionally terminated, the processor 130 may perform control to output the user interface including a display object or the voice information which notifies a user of the unintentional termination. Furthermore, the processor 130 may execute the exercise application 113 in response to a selection of the display object and may display a screen configured according to the exercise history information including information obtained from when the exercise application 113 was first executed to when the exercise application was unintentionally terminated.

The memory 150 may store instructions or data related to at least one other component included in the electronic device 100. According to an embodiment of the present disclosure, the memory 150 may store the exercise history information. For example, the memory 150 may store the exercise time, the exercise information, the real-time exercise data, the exercise progress rate, or the like. Furthermore, the memory 150 may store information related to the unintentional termination of the exercise service provided by the exercise service module 110. For example, the memory 150 may store completion indicating information which makes it possible for the processor 130 to determine whether the stored exercise history information is exercise history information of a completed exercise, together with the information related to the unintentional termination of the exercise service. According to an embodiment of the present disclosure, the memory 150 may store software and/or an application program. For example, the memory 150 may include the exercise history information managing service module 111 and the exercise application 113.

The sensor 170 may measure a physical quantity or may sense an object. The sensor 170 may include at least one of a gyro sensor or an acceleration sensor. The sensor 170 may collect sensor information corresponding to a position change of the electronic device 100. According to various embodiments of the present disclosure, the sensor 170 may collect sensor information corresponding to the position change of the electronic device 100, as a result of the electronic device 100 being moved while a user is performing the exercise. According to various embodiments of the present disclosure, the sensor 170 may include one or more other sensors in addition to the above-mentioned gyro sensor or acceleration sensor. For example, the sensor module 170 may further include a geomagnetic sensor.

According to various embodiments of the present disclosure, the electronic device 100 may include an exercise history information managing service module 111 for recording exercise history information about a specific exercise even when an exercise application which provides a user interface about the specific exercise is abnormally terminated and the memory 150 for storing the exercise history information.

According to various embodiments of the present disclosure, the abnormal termination of the exercise application 113 may include at least one of where the exercise application is forcibly terminated in a memory shortage status, where the exercise application is forcibly terminated due to an error of the exercise application, where the exercise application is forcibly terminated by an application managing module, and where the user terminates the exercise application arbitrarily and forcibly.

According to various embodiments of the present disclosure, the exercise history information may include at least one of an exercise time, basic exercise information, real-time exercise data, or an exercise progress rate.

According to various embodiments of the present disclosure, the exercise history information managing service module 111 may perform control to output at least one of a display object or voice information to notify of the abnormal termination of the exercise application 113 during the exercise.

According to various embodiments of the present disclosure, the exercise history information managing service module 111 may execute the exercise application 113 in response to a selection of the display object and may perform control to configure and display a screen about the exercise application 113 based on the exercise history information relating to the exercise.

According to various embodiments of the present disclosure, the exercise history information managing service module 111 may perform control to configure and display a screen of the exercise application based on the exercise history information relating to the exercise when the exercise application is first executed after the exercise application is abnormally terminated.

According to various embodiments of the present disclosure, the exercise history information managing service module 111 may perform control to display an object which guides to determine whether to restart the exercise when the exercise application is first executed after the exercise application is abnormally terminated.

According to various embodiments of the present disclosure, the exercise history information managing service module 111 may perform control to delete the exercise history information when the restart of the exercise is cancelled.

According to various embodiments of the present disclosure, the exercise history information managing service module 111 may perform control to configure and display a screen, which is the same as or similar to a screen displayed at a point in time when the exercise application is abnormally terminated, based on the exercise history information when the restart of the exercise is selected.

According to various embodiments of the present disclosure, the exercise history information managing service module 111 may perform control to output at least one of a display object or voice information corresponding to comprehensive information of the exercise based on the exercise history information, at a point in time of the termination of the exercise after the exercise restarts or at a point in time when the exercise history information is displayed after the exercise restarts.

According to various embodiments of the present disclosure, in the case where the exercise application 113 and the exercise history information managing service module 111 are abnormally terminated, the electronic device 100 may perform control to output at least one of the display object or the voice information to notify a user of the abnormal termination of the exercise application 113 and the exercise history information managing service module 111. In this regard, the case where the exercise application 113 and the exercise history information managing service module 111 are abnormally terminated may include at least one, where the user arbitrarily replaces the battery in a low battery condition, where the electronic device is powered off due to battery discharge, where the exercise application is forcibly terminated in a memory shortage status, where the exercise application is forcibly terminated due to an error of the exercise application 113, where the exercise application 113 or the exercise history information managing service module 111 is forcibly terminated by the application managing module, where the user arbitrarily terminates the exercise application 113, or where a battery separation, a power-off, a malfunction, or the like occurs due to the user's negligence.

According to various embodiments of the present disclosure, the electronic device 100 may execute the exercise application 113 in response to the selection of the display object and may perform control to configure and display the screen relating to the exercise application 113 based on the exercise history information relating to the exercise. Furthermore, the electronic device 100 may perform control to configure and display the screen about the exercise application 113 based on the exercise history information relating to the exercise in response to a first execution of the exercise application after the exercise application 113 and the exercise history information managing service module 111 are abnormally terminated. According to an embodiment of the present disclosure, the electronic device 100 may perform control to display the object, which guides to determine whether to restart the exercise when the exercise application 113 is first executed, after the exercise application 113 and the exercise history information managing service module 111 are unintentionally terminated. In this case, the electronic device 100 may perform control to delete the exercise history information when the restart of the exercise is cancelled. Furthermore, in the case where the restart of the exercise is selected, the electronic device 100 may perform control to configure and display a screen which is the same as or similar to a screen displayed at a point in time when the exercise application 113 is abnormally terminated based on the exercise history information. According to various embodiments of the present disclosure, at a point in time when the exercise is terminated after the restart or at a point in time when the exercise history information is displayed with regard to the exercise after the restart, the electronic device 100 may perform control to output at least one of the display object or the voice information corresponding to information of the exercise, based on the exercise history information.

Figure 2:
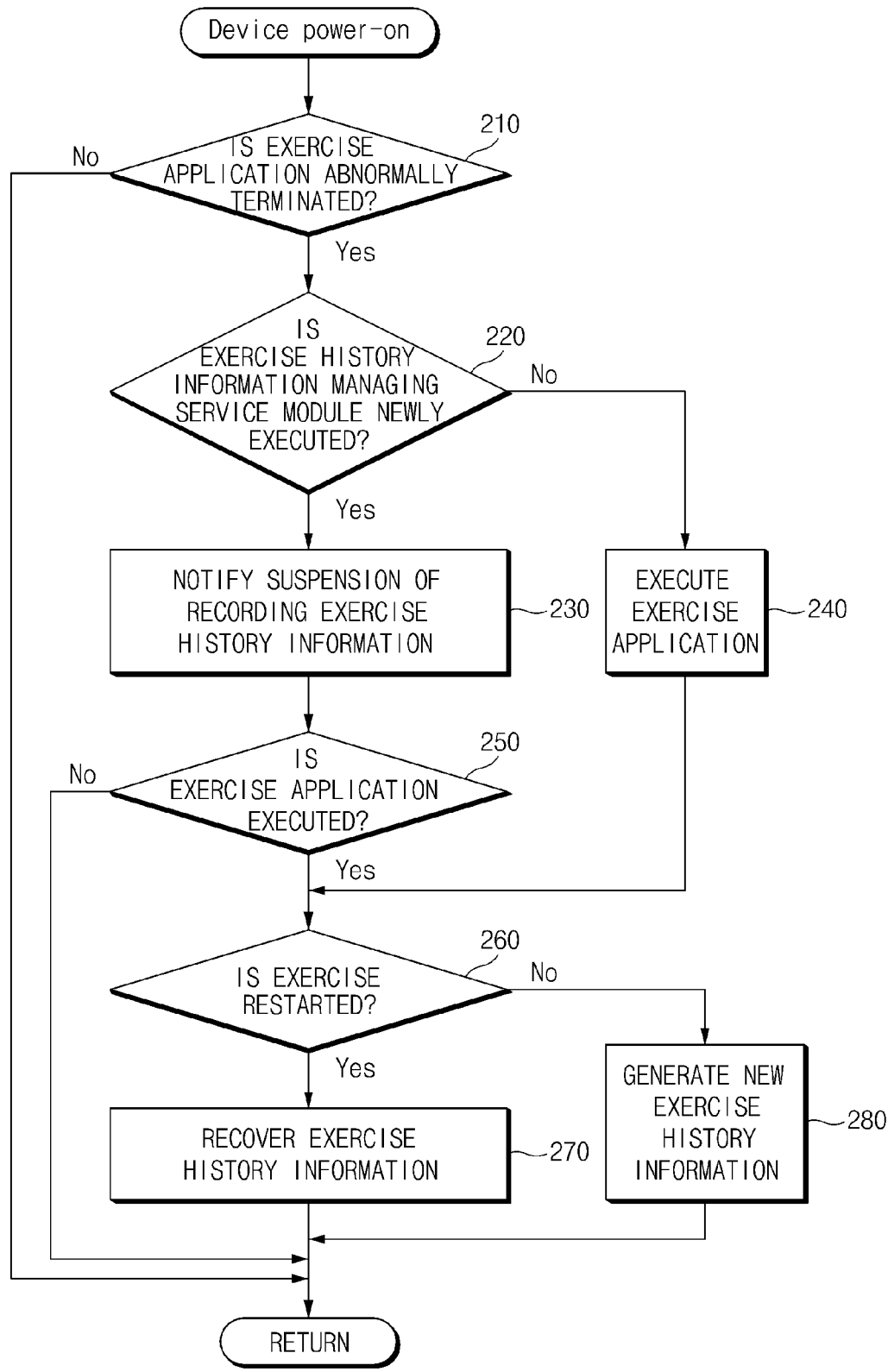
FIG. 2 is a flowchart illustrating a method of an electronic device which provides exercise history information, according to an embodiment of the present disclosure.

FIG. 2 is a flowchart illustrating a method of the electronic device 100 which provides exercise history information, according to an embodiment of the present disclosure. The electronic device 100 may provide a method for preventing a discontinuity of the exercise history information due to the unintentional termination of the exercise service provided by the exercise service module 110. In the electronic device 100, a degree and method for providing the exercise history information may vary according to a termination of a component included in the exercise service module 110. For example, in the case where only the exercise application 113 is unintentionally terminated while a user is performing the exercise, the electronic device 100 may continuously record the exercise history information through the exercise history information managing service module 111. Furthermore, the electronic device 100 may output the user interface including the display object or the voice object for notifying a user using information relating to the exercise status and/or the unintentional termination of the exercise application 113.

According to an embodiment of the present disclosure, in the case where the exercise history information managing service module 111, as well as the exercise application 113, is/are unintentionally terminated while a user is performing the exercise, the electronic device 100 may output the user interface including the display object or the voice object for notifying a user of the unintentional termination of the exercise service provided by the exercise service module 110. According to various embodiments of the present disclosure, the electronic device 100 may configure and display the screen which is the same as or similar to the screen that was displayed on the electronic device 100 just before the unintentional termination of the exercise service based on the corresponding exercise history information along with the notification of the unintentional termination of the exercise service while the user is performing the exercise.

Referring to FIG. 2, in operation 210, the electronic device 100 may determine whether the exercise application 113 has been abnormally/unintentionally terminated after a power-on. For example, in the case where there is exercise history information, which does not have the completion indicating information, among the exercise history information stored in the memory 150 in FIG. 1, the electronic device 100 may determine that the exercise application 113 has been unintentionally terminated. The completion indicating information may be information which is set in the case where the goal of the specific exercise has been achieved with regard to the performance of the specific exercise service provided from the exercise application 113. In this regard, the electronic device 100 may store the completion indicating information together with the corresponding exercise history information in the memory 150.

In the case where the exercise application 113 is unintentionally terminated, in operation 220, the electronic device 100 may determine whether the exercise history information managing service module 111 is newly executed. For example, the electronic device 100 may determine whether the exercise history information managing service module 111 is newly executed by determining whether the service ID assigned to the execution of the exercise history information managing service module 111 is changed.

In the case where the exercise history information managing service module 111 is newly executed, in operation 230, the electronic device 100 may display information to a user indicating that recording of the exercise history information is suspended. For example, the electronic device 100 may display information to a user indicating that recording of the exercise history information is suspended due to the unintentional termination of the exercise application 113 while the user is performing the exercise. According to an embodiment of the present disclosure, the electronic device 100 may display the user interface and/or the display object, which includes an image, text, or the like, which notifies a user of the suspension of recording of the exercise history information on a quick panel, for example, a screen displayed by pressing and dragging downwards the upper area of the screen of the electronic device 100.

In the case where the exercise history information managing service module 111 is not newly executed, in operation 240, the electronic device 100 may execute the exercise application 113. According to various embodiments of the present disclosure, in operation 230, the electronic device 100 may display the status in which recording of the exercise history information is suspended on the quick panel. The electronic device 100 may guide the user to execute the exercise application 113 by displaying the suspension status of the recording of the exercise history information.

In operation 250, the electronic device 100 may determine whether the exercise application 113 is executed. If the exercise application 113 is executed, in operation 260, the electronic device 100 may determine whether to restart the suspended exercise service relating to the exercise. According to an embodiment of the present disclosure, the electronic device 100 may display the user interface including an object including a button or the like which guides the user to select whether to restart the exercise relating to the exercise service along with the exercise history information relating to the suspended exercise. The exercise history information relating to the suspended exercise may include information such as an exercise time, a kind of the exercise, an intensity of the exercise, a frequency of the exercise, an exercise distance, a calorie consumption, or the like related to the corresponding exercise stored in the memory 150.

If the user elects to the restart the exercise relating to the exercise service (e.g., the user selects a button object indicating selection of the restart of the exercise), in operation 270, the electronic device 100 may deliver the exercise history information to the exercise application 113. Furthermore, the exercise application 113 may configure and display a screen which is the same as or similar to a screen that was displayed at a point in time when the exercise service was suspended, by recovering the exercise history information.

If the user elects not to restart the exercise relating to the exercise service (e.g., the user selects a button object indicating canceling of the restart of the exercise), in operation 280, the electronic device 100 may control to generate exercise history information corresponding to a new exercise and a new exercise service. In this case, the electronic device 100 may delete the exercise history information relating to the suspended exercise service to secure a space in the memory 130 for information relating to the new exercise and the new exercise service. Alternatively, the electronic device 100 may set the completion indicating information about the suspended exercise service such that the new exercise service is not recognized as the suspended exercise service.

As described above, even though the exercise service is unintentionally terminated, the electronic device 100 may guarantee the continuity of the exercise history information through the exercise history information managing service module 111, which is set to manage the exercise history information relating to the corresponding exercise. Furthermore, the electronic device 100 may provide the user interface so that the user can perform the suspended exercise in a relatively continuous manner. For example, the electronic device 100 may configure and display the screen such that the suspended exercise has a continuity based on the exercise history information. Alternatively, the electronic device 100 may output the display object or the voice information for notifying a user of the suspension of the exercise service.

According to various embodiments of the present disclosure, the exercise history information managing service module 111 may monitor a status of the electronic device 100 while a user is performing an exercise in real time. For example, the exercise history information managing service module 111 may monitor the state of charge, the memory usage and remaining capacity, and the like of the electronic device 100 while a user is performing the exercise. According to an embodiment of the present disclosure, in the case where it is determined that the exercise service may be unintentionally terminated based on the above-mentioned status of the electronic device 100, the exercise history information managing service module 111 may output the display object and/or the voice information corresponding to the status information of the electronic device 100. For example, the exercise history information managing service module 111 may output the display object or the voice information corresponding to the state of charge and a minimum possible exercise time while the user is performing the exercise. Furthermore, the exercise history information managing service module 111 may calculate the remaining capacity and the expected usage of the memory 150 during the exercise, and if a usable capacity of the memory 150 is insufficient, the exercise history information managing service module 111 may output the display object or the voice information to notify a user of the lack of capacity in the memory 150.

Figure 3:
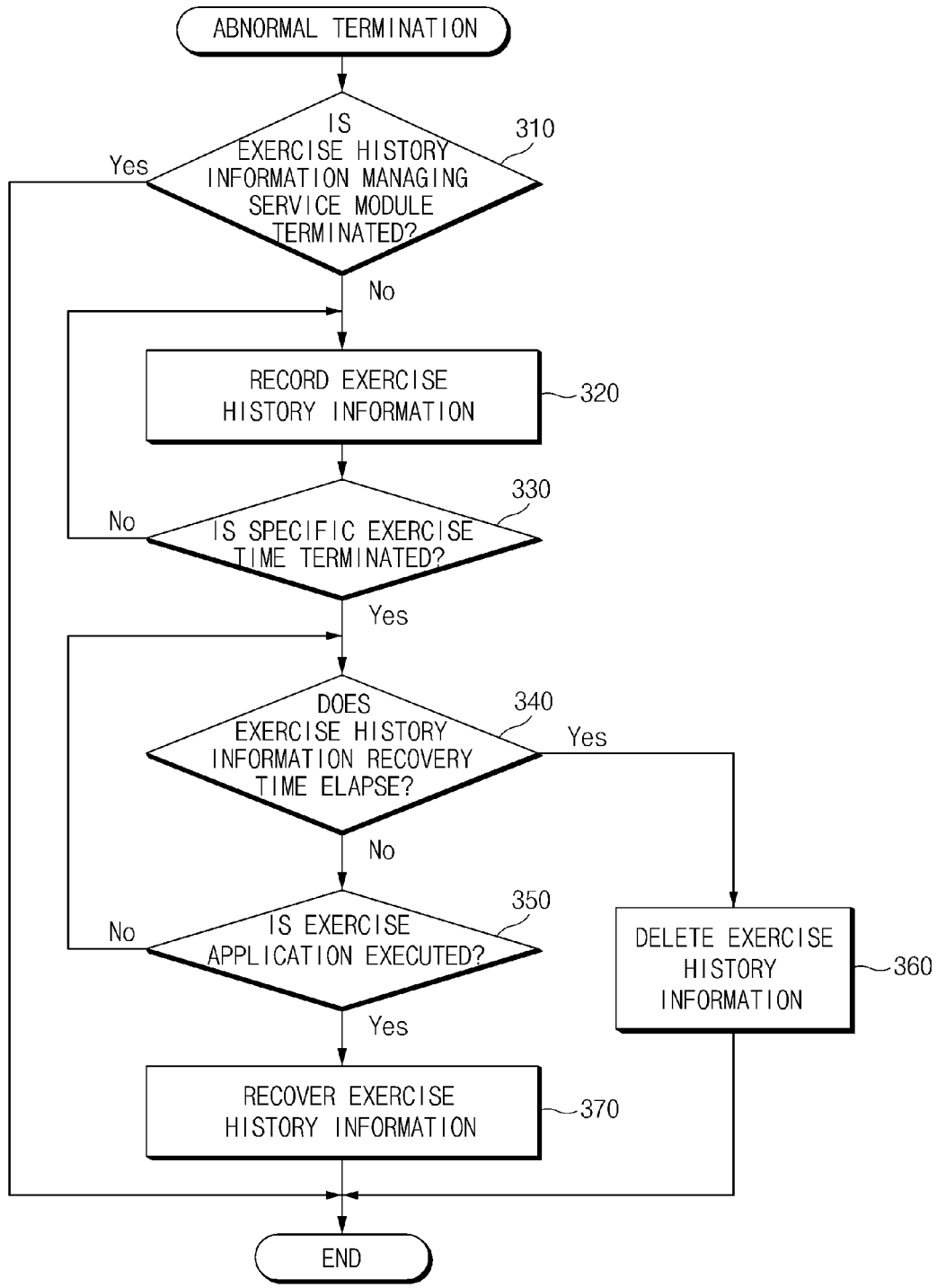
FIG. 3 is a flowchart illustrating a method of an electronic device when an exercise service is unintentionally terminated, according to an embodiment of the present disclosure.

FIG. 3 is a flowchart illustrating a method of the electronic device 100 when an exercise service is unintentionally terminated, according to an embodiment of the present disclosure. The exercise service of the electronic device 100 may be unintentionally terminated under several conditions while the electronic device 100 is obtaining the exercise history information. For example, the exercise service of the electronic device 100 may be unintentionally terminated under several conditions, such as when the user arbitrarily replaces the battery of the electronic device 100 in a low battery condition, when the electronic device 100 is powered-off due to the battery discharge, when the exercise application 113 is forcibly terminated to protect the highest level application in a status of a low memory, when the exercise application 113 is forcibly terminated due to an error of the exercise application 113, when the exercise application 113 is forcibly terminated by the application managing module, the case where the user arbitrarily terminates the exercise application 113, or when a battery separation, a power-off, a malfunction, or the like occurs due to the user's negligence.

Referring to FIG. 3, in the case where the unintentional termination occurs as described above, in operation 310, the electronic device 100 may determine whether the exercise history information managing service module 111 is terminated. If the exercise history information managing service module 111 is not terminated, in operation 320, the electronic device 100 may continuously record the exercise history information. For example, the electronic device 100 may collect a sensing value from the sensor 170 based on the exercise being performed by the user and may record the exercise data in real time.

In operation 330, the electronic device 100 may determine whether a specific exercise time, which corresponds to an exercise, is terminated (or has elapsed) and may record the exercise data in real time during the specific exercise time. If the specific exercise time is terminated, in operation 340, the electronic device 100 may determine whether an exercise history information recovery time relating to the corresponding exercise elapses. According to an embodiment of the present disclosure, the electronic device 100 may set the exercise history information recovery time differently based on a cause of the unintentional termination of the exercise service. For example, in the case where the user arbitrarily replaces the battery in the low-battery status and the user arbitrarily performs a forcible termination of the exercise application 113, the electronic device 100 may set the exercise history information recovery time to 30 minutes. Furthermore, the electronic device 100 may set the exercise history information recovery time to 3 hours in cases where the electronic device 100 is powered-off due to the battery discharge, where the exercise application 113 is forcibly terminated to protect the highest level application in a status of a low memory, where the exercise application is forcibly terminated due to an error of the exercise application 113, where the exercise application 113 is forcibly terminated by the application managing module, where the user arbitrarily terminates the exercise application 113, and where a battery separation, a power-off, a malfunction, or the like occurs due to the user's negligence. However, the present disclosure is not limited to 30 minutes and 3 hours as described above, as such time limits are merely provided for illustrative purposes. As can be appreciated, the time limits can be less than 30 minutes, between 30 minutes and 3 hours, or greater than 3 hours.

If the exercise history information recovery time elapses, in operation 360, the electronic device 100 may delete the corresponding exercise history information to secure space in the memory 150. If the exercise history information recovery time does not elapse, in operation 350, the electronic device 100 may determine whether the exercise application 113 is executed. If the exercise application 113 is executed, in operation 370, the electronic device 100 may perform control to recover and display the exercise history information, which is the exercise history information just before the unintentional termination. In this case, the electronic device 100 may configure and display the screen which is the same as or similar to the screen which is displayed just before the unintentional termination of the exercise application 113 based on the exercise history information. Furthermore, after the unintentional termination of the exercise application 113, the electronic device 100 may provide exercise history information that is collected through the exercise history information managing service module 111 after the unintentional termination of the exercise application 113, and the exercise history information collected just prior to the unintentional termination of the exercise application 113.

According to various embodiments of the present disclosure, a method for managing exercise history information in the electronic device 100 may include recording exercise history information relating to an exercise even when an exercise application 113 which provides a user interface about the specific exercise is abnormally terminated and storing the exercise history information.

According to various embodiments of the present disclosure, the recording of the exercise history information may include recording the exercise history information at at least one of a point in time of a forcible termination of the exercise application 113 in a memory shortage status, a point in time of a forcible termination due to an error of the exercise application 113, a point in time of a forcible termination of the exercise application 113 by an application managing module, or a point in time of an arbitrary, forcible termination of the exercise application 113 by a user.

According to various embodiments of the present disclosure, the exercise history information may include at least one of an exercise time, exercise information, real-time exercise data, or an exercise progress rate in the exercise history information.

According to various embodiments of the present disclosure, the recording of the exercise history information may further include performing control to output at least one of a display object or voice information for notifying a user of the unintentional termination of the exercise application 113 at the abnormal termination of the exercise application 113 while a user is performing the exercise.

According to various embodiments of the present disclosure, the performing of the control to output the at least one of the display object or the voice information may further include executing the exercise application 113 in response to a selection of the display object and performing control to configure and display a screen relating to the exercise application 113 based on the exercise history information.

According to various embodiments of the present disclosure, the recording of the exercise history information may further include performing control to configure and display a screen relating to the exercise application 113 based on the exercise history information when the exercise application 113 is first executed after the exercise application 113 is unintentionally terminated.

According to various embodiments of the present disclosure, the recording of the exercise history information may further include performing control to display an object which guides a user to determine whether to restart the exercise when the exercise application 113 is first executed after the exercise application 113 is unintentionally terminated.

According to various embodiments of the present disclosure, the performing of the control to display the object may further include deleting the exercise history information when the restart of the exercise is cancelled.

According to various embodiments of the present disclosure, the performing of the control to display the object may further include performing control to configure and display a screen, which is the same as or similar to a screen displayed when the exercise application 113 is abnormally terminated, based on the exercise history information in the case where the restart of the exercise is selected.

According to various embodiments of the present disclosure, the performing of the control to configure and display the screen may further include performing control to output at least one of a display object or voice information corresponding to comprehensive information of the exercise based on the exercise history information, at a point in time when the exercise is terminated after the exercise restarts or at a point in time when the exercise history information is displayed after the exercise restarts.

Figure 4:
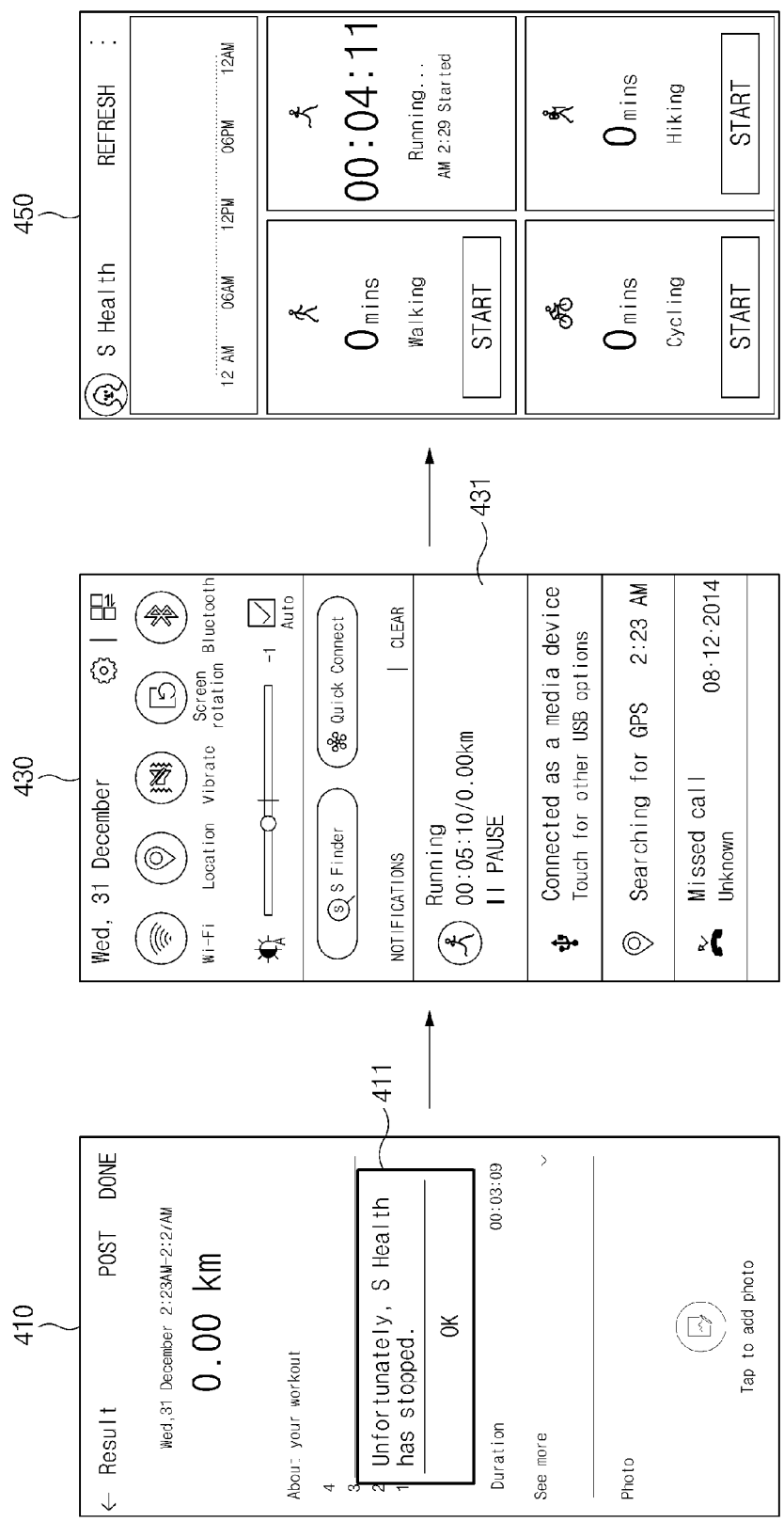
FIG. 4 is a diagram illustrating an example of a screen that provides exercise history information, according to an embodiment of the present disclosure.

FIG. 4 is a diagram illustrating an example of a screen that provides exercise history information, according to an embodiment of the present disclosure.

Referring to FIG. 4, the electronic device 100 displays an unintentional termination screen 410 when the exercise service is unintentionally terminated. In the case where the unintentional termination screen 410 is displayed, the electronic device 100 may display a display object 411 (e.g., a pop-up window), which includes information about a cause of the unintentional termination, on a specific area in the screen. In the case where a specific time elapses or an object (e.g., a specific button) included in the display object is selected, outputting of the display object 411, which is displayed for notifying a user of the cause of the termination at the time of the unintentional termination, may be stopped.

In the case where the exercise application 113 is unintentionally terminated, but the exercise history information managing service module 111 is not terminated, the electronic device 100 may continuously record the exercise history information even though the exercise service is unintentionally terminated. For example, the electronic device 100 may record the real-time exercise data using a sensing value related to the exercise, which is collected from the sensor 170 through the exercise history information managing service module 111. Furthermore, the electronic device 100 may display a screen 430 to notify a user that the exercise history information is being continuously recorded. According to an embodiment of the present disclosure, the electronic device 100 may display the screen 430 on the quick panel. The electronic device 100 may display a display object 431, which includes an image, a text, or the like corresponding to information related to the corresponding exercise, for example a kind of the exercise, an exercise time, an exercise distance, an exercise status, or the like, on a specific area of the screen 430.

According to various embodiments of the present disclosure, the electronic device may execute the exercise application 113 in response to a selection of the display object 431. Furthermore, the electronic device 113 may recover the exercise history information collected through the exercise history information managing service module 111 and may display a screen 450 of the exercise application 113. The screen 450 may be configured differently based on whether the corresponding exercise is terminated. For example, before the corresponding exercise is terminated, the screen 450 may have the configuration which is the same as or similar to that of the screen at a point in time of the unintentional termination of the exercise application 113 and may be updated according to the exercise history information collected through the exercise history information managing service module 111. In the case where the corresponding exercise is terminated in excess of the specific exercise time, the screen 450 may display an image, a text, or the like corresponding to comprehensive information relating to the corresponding exercise based on the collected exercise history information. The comprehensive information may include a kind of exercise, a total exercise time, a total exercise distance, a total calorie consumption, or the like.

Figure 5:
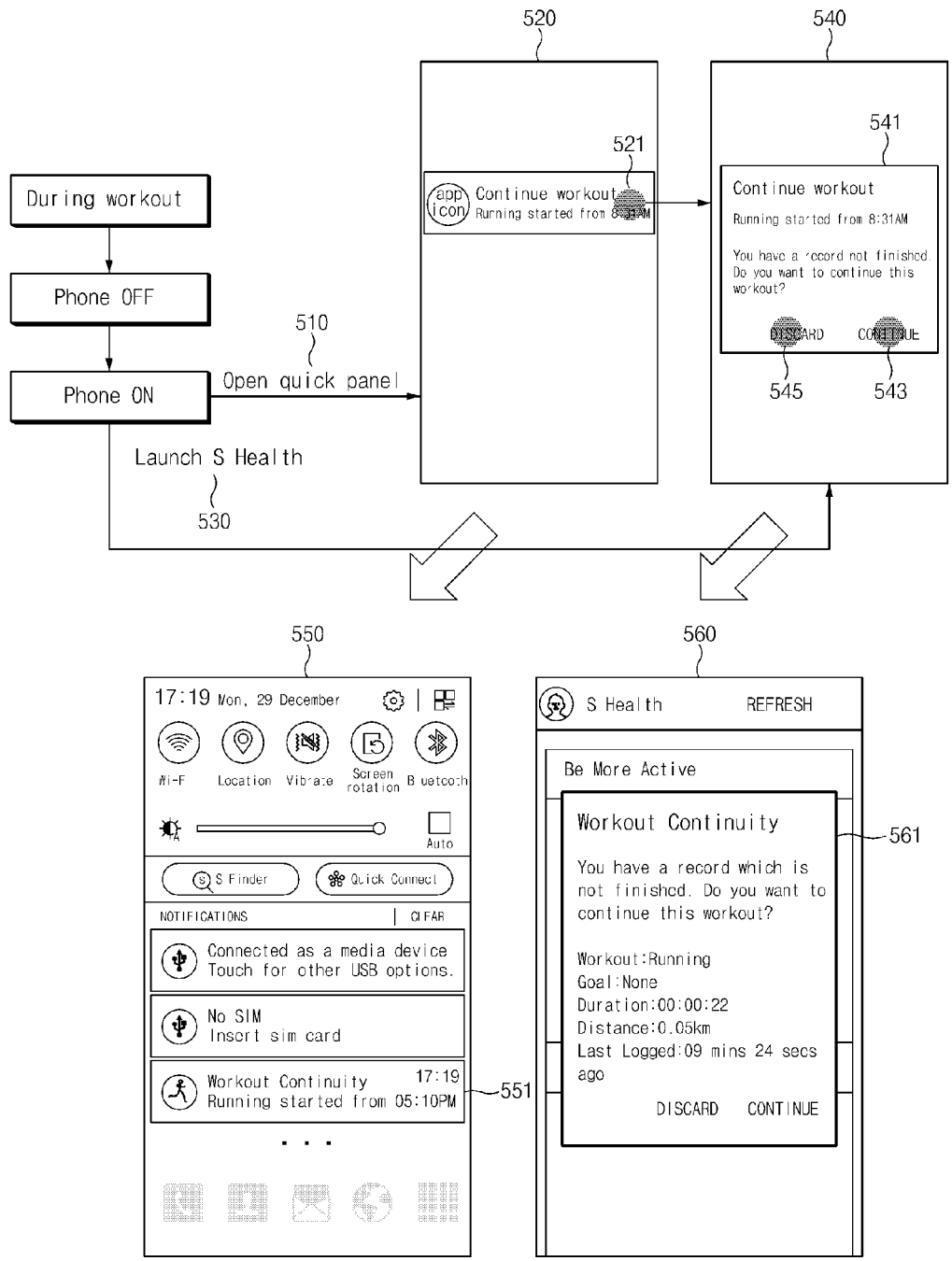
FIG. 5 is a diagram illustrating an example of a screen that notifies a user of a suspension of exercise history information, according to an embodiment of the present disclosure.

FIG. 5 is a diagram illustrating an example of a screen that notifies a user of a suspension of exercise history information, according to an embodiment of the present disclosure.

Referring to FIG. 5, the electronic device 100 may display a screen which notifies a user of the suspension of the exercise history information when the unintentional termination (e.g., power off of the electronic device 100) of the exercise service is occurred while a user is performing the exercise. According to an embodiment of the present disclosure, in the case where the power is turned-off and then turned-on while the exercise history information is being collected, the electronic device 100 may determine whether there is exercise history information which does not have the completion indicating information among the exercise history information stored in the memory 150 to determine whether the exercise service is unintentionally terminated. In the case where there is exercise history information which does not have the completion indicating information, the electronic device 100 may display the screen to notify a user of the suspension of the exercise history information. As illustrated by reference number 510, an open quick panel command may be generated by for displaying a display object 521 for notifying a user of the suspension of the exercise history information on a specific area of a quick panel screen 520. The display object 521 may include an image, a text, or the like corresponding to information of the corresponding exercise, for example an icon of the exercise application, a kind of the exercise, an exercise starting time, and the like. A screen 550 is one example of the quick panel screen 520, and the display object 551 may be an example of the display object 521, which displays information relating to a corresponding exercise. According to an embodiment of the present disclosure, the electronic device 100 may execute the exercise application 113 in response to a selection of the display object 521/551.

According to various embodiments of the present disclosure, in the case where the exercise application 113 is executed again after the unintentional termination of the exercise service, the electronic device 100 may display the screen which notifies a user of the suspension of the exercise history information. For example, the electronic device 100 may display the display object 541 which notifies a user of the suspension of the exercise history information on a specific area of the start screen (or execution screen) 540 of the exercise application 113 in response to the execution of the exercise application 113. The display object 541 may include an image, a text, or an object which includes a button or the like to guide a user for determining whether to restart of the corresponding exercise service corresponding to the information of the corresponding exercise. For example, the display object 541 may include a button 543 for restarting the corresponding exercise and a button 545 for not restarting the corresponding exercise. According to various embodiments of the present disclosure, if the button 543 is selected, the electronic device 100 may recover the corresponding exercise history information and may configure and display the screen which is the same as or similar to the screen of the exercise application at a point in time of the unintentional termination of the exercise service. If the button 545 is selected, the electronic device 100 may delete the corresponding exercise history information and may configure and display a screen for a new exercise. A screen 560 is one example of the screen 540, and the display object 561 may be an example of the display object 541. The screen 560 illustrates that the display object 561 is displayed on a specific area in the form of pop-up.

Figure 6:
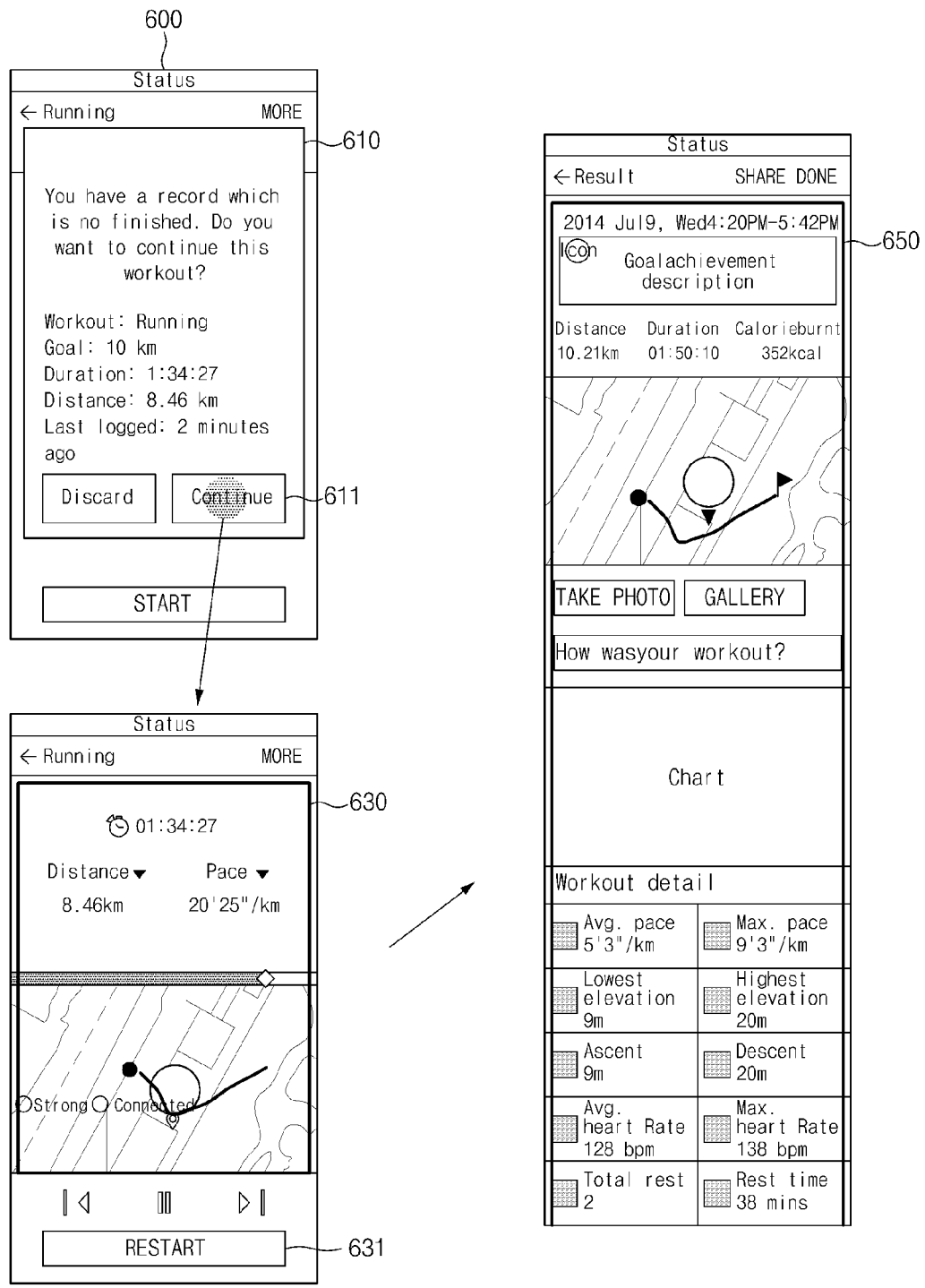
FIG. 6 is a diagram illustrating an example of a screen that displays exercise history information when an exercise restarts, according to an embodiment of the present disclosure.

FIG. 6 is a diagram illustrating an example of a screen that displays exercise history information when an exercise restarts, according to an embodiment of the present disclosure.

Referring to FIG. 6, in the case where the exercise service is unintentionally terminated, the electronic device 100 may display a display object 610 which notifies a user of the suspension of the exercise history information on a specific area of a start screen (or execution screen) 600 of the exercise application 113. According to an embodiment of the present disclosure, in the case where the exercise application 113 is executed again in the state where the power of the electronic device 100 is turned-off and then turned-on again due to the unintentional termination of the exercise service, the electronic device 100 may display a display object 610 which notifies a user of the suspension of the exercise history information. The display object 610 may include a kind of the exercise, an exercise time, an exercise distance, an exercise goal, a last stored exercise history information time, a discard button of an exercise restart, an exercise restart button 611, and the like based on the corresponding exercise history information.

If the exercise restart button 611 is selected, the electronic device 100 may recover the corresponding exercise history information and may configure and display a screen 630 which is the same as or similar to the screen of the exercise application 113 at a point in time of the abnormal termination of the exercise service. The screen 630 may include an image, a text, or the like corresponding to the recovered exercise history information. According to an embodiment of the present disclosure, the electronic device 100 may display map data on a specific area of the screen 630 which includes location information relating to the exercise path based on the recovered exercise history information. Furthermore, the electronic device 100 may display the button 631 which determines the exercise restart on an area adjacent to the screen 630.

In the case where the user terminates the corresponding exercise after selecting the button 631, the electronic device 100 may display a screen 650 corresponding to comprehensive exercise information based on the exercise history information of the corresponding exercise at a point in time of the termination of the corresponding exercise or at a point in time of displaying exercise history information with regard to the corresponding exercise. The screen 650 may include an image, a text, or the like corresponding to information such as an exercise date, an exercise time, an exercise distance, a total calorie consumption, an exercise path, exercise detailed information, or the like. According to various embodiments of the present disclosure, the electronic device 100 may perform control to output the voice information corresponding to the above-mentioned exercise information. According to an embodiment of the present disclosure, in the case where a specific area of the screen 650 is outside of a display area, the electronic device 100 may support to display the area which is not currently displayed in response to a scroll operation of a scroll bar configured in a specific area of the screen 650.

Figure 7:
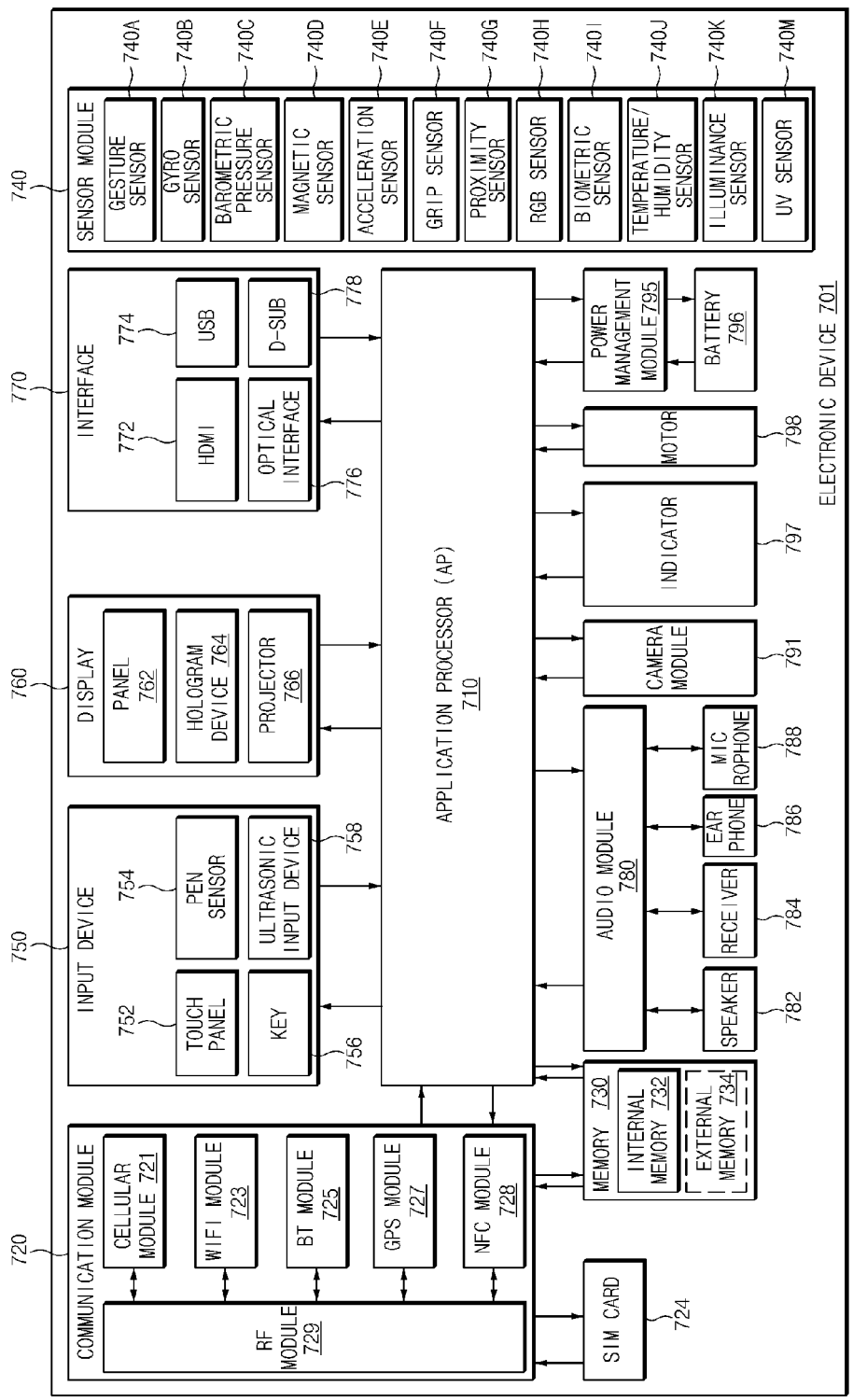
FIG. 7 is a diagram illustrating an electronic device, according to an embodiment of the present disclosure.

FIG. 7 is a diagram illustrating an electronic device, according to an embodiment of the present disclosure.

Referring to FIG. 7, an electronic device 701 may include, for example, some or all of the components of the electronic device 100 illustrated in FIG. 1. The electronic device 701 may include one or more processors (e.g., an AP, a graphics processor, and the like) 710, a communication module 720, a subscriber identification module (SIM) 724, a memory 730, a sensor module 740, an input device 750, a display 760, an interface 770, an audio module 780, a camera module 791, a power management module 795, a battery 796, an indicator 797, and a motor 798.

The processor 710 may drive an operating system (OS) or an application to control a plurality of hardware or software components connected to the processor 710 and may process and compute a variety of data. The processor 710 may be implemented with a system on chip (SoC), for example. According to an embodiment of the present disclosure, the processor 710 may further include a graphic processing unit (GPU) and/or an image signal processor. The processor 710 may include at least a part (e.g., a cellular module 721) of components illustrated in FIG. 7. The processor 710 may load and process an instruction or data, which is received from at least one of other components, onto a nonvolatile memory and may store a variety of data at the nonvolatile memory.

The communication module 720 may be configured the same as or similar to conventional communication modules. The communication module 720 may include a cellular module 721, a wireless-fidelity (Wi-Fi) module 723, a bluetooth (BT) module 725, a global positioning system (GPS) module 727, a near field communication (NFC) module 728, and a radio frequency (RF) module 729.

The cellular module 721 may provide voice communication, video communication, a character service, an Internet service or the like through a communication network. According to an embodiment of the present disclosure, the cellular module 721 may perform discrimination and authentication of an electronic device 701 within a communication network using the SIM 724, for example. According to an embodiment of the present disclosure, the cellular module 721 may perform at least a portion of functions that the processor 710 provides. According to an embodiment of the present disclosure, the cellular module 721 may include a communication processor (CP).

Each of the Wi-Fi module 723, the BT module 725, the GPS module 727, and the NFC module 728 may include a processor for processing data exchanged through a corresponding module. According to an embodiment of the present disclosure, at least a portion (e.g., two or more components) of the cellular module 721, the Wi-Fi module 723, the BT module 725, the GPS module 727, and the NFC module 728 may be included within one integrated circuit (IC) or an IC package.

The RF module 729 may transmit and receive a communication signal (e.g., an RF signal). The RF module 729 may include a transceiver, a power amplifier module (PAM), a frequency filter, a low noise amplifier (LNA), an antenna, or the like. According to various embodiments of the present disclosure, at least one of the cellular module 721, the Wi-Fi module 723, the BT module 725, the GPS module 727, or the NFC module 728 may transmit and receive an RF signal through a separate RF module.

The SIM 724 may include unique identify information (e.g., integrated circuit card identifier (ICCID)) or subscriber information (e.g., integrated mobile subscriber identity (IMSI)).

The memory 730 may include an internal memory 732 or an external memory 734. For example, the internal memory 732 may include at least one of a volatile memory (e.g., a dynamic random access memory (DRAM), a static RAM (SRAM), or a synchronous DRAM (SDRAM)), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a NAND flash memory, or a NOR flash memory), a hard drive, or a solid state drive (SSD).

The external memory 734 may include a flash drive, for example, compact flash (CF), secure digital (SD), micro secure digital (Micro-SD), mini secure digital (Mini-SD), extreme digital (xD), multimedia card (MMC), a memory stick, or the like. The external memory 734 may be functionally and/or physically connected to the electronic device 701 through various interfaces.

The sensor module 740 may measure, for example, a physical quantity or may detect an operation state of the electronic device 701. The sensor module 740 may convert the measured or detected information to an electric signal. The sensor module 740 may include at least one of a gesture sensor 740A, a gyro sensor 740B, a barometric pressure sensor 740C, a magnetic sensor 740D, an acceleration sensor 740E, a grip sensor 740F, a proximity sensor 740G a color sensor 740H (e.g., red, green, blue (RGB) sensor), a biometric sensor 740I, a temperature/humidity sensor 740J, an illuminance sensor 740K, or an ultra violet (UV) sensor 740M. Although not illustrated, the sensor module 740 may further include, for example, an e-nose sensor, an electromyography sensor (EMG) sensor, an electroencephalogram (EEG) sensor, an electrocardiogram (ECG) sensor, a photoplethysmographic (PPG) sensor, an infrared (IR) sensor, an iris sensor, and/or a fingerprint sensor. The sensor module 740 may further include a control circuit for controlling at least one or more sensors included therein. According to an embodiment of the present disclosure, the electronic device 701 may further include a processor which is a part of the processor 710 or independent from the processor 710 and is configured to control the sensor module 740. The processor may control the sensor module 740 while the processor 710 remains in a sleep state.

The input device 750 may include, for example, a touch panel 752, a (digital) pen sensor 754, a key 756, or an ultrasonic input device 758. The touch panel 752 may use at least one of capacitive, resistive, infrared and ultrasonic detecting methods. Also, the touch panel 752 may further include a control circuit. The touch panel 752 may further include a tactile layer to provide a tactile reaction to a user.

The (digital) pen sensor 754 may be, for example, a part of a touch panel or may include an additional sheet for recognition. The key 756 may include, for example, a physical button, an optical key, a keypad, and the like. The ultrasonic input device 758 may detect (or sense) an ultrasonic signal, which is generated from an input device, through a microphone 788 and may check data corresponding to the detected ultrasonic signal.

The display 760 may include a panel 762, a hologram device 764, and a projector 766. The panel 762 may be configured the same as or similar to conventional displays. The panel 762 and the touch panel 752 may be integrated into a single module. The hologram device 764 may display a stereoscopic image in a space using a light interference phenomenon. The projector 766 may project light onto a screen to display an image. The screen may be arranged inside or outside of the electronic device 701. According to an embodiment of the present disclosure, the display 760 may further include a control circuit for controlling the panel 762, the hologram device 764, and/or the projector 766.

The interface 770 may include, for example, a high-definition multimedia interface (HDMI) 772, a universal serial bus (USB) 774, an optical interface 776, or a D-sub-miniature (D-sub) 778. Additionally or alternatively, the interface 770 may include, for example, a mobile high definition link (MHL) interface, a SD card/multi-media card (MMC) interface, and/or an infrared data association (IrDA) standard interface.

The audio module 780 may convert a sound and an electric signal bi-directionally. The audio module 780 may process, for example, sound information that is input or output through a speaker 782, a receiver 784, an earphone 786, or the microphone 788.

The camera module 791, which is used for shooting a still image or a video, may include, for example, at least one image sensor (e.g., a front sensor or a rear sensor), a lens, an image signal processor (ISP), or a flash (e.g., a light emitting diode (LED) or a xenon lamp).

The power management module 795 may manage, for example, power of the electronic device 701. According to an embodiment of the present disclosure, a power management integrated circuit (PMIC) a charger IC, or a battery gauge may be included in the power management module 795. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, or a rectifier, and the like. The battery gauge may measure, for example, a remaining capacity of the battery 796 and a voltage, current or temperature thereof while the battery is charged. The battery 796 may include, for example, a rechargeable battery or a solar battery.

The indicator 797 may display a specific state of the electronic device 701 or a portion thereof (e.g., a processor 710), such as a booting state, a message state, a charging state, and the like. The motor 798 may convert an electrical signal into a mechanical vibration and may generate one or more effects including, but not limited to, vibration, haptic, and the like. Although not illustrated, a processing device (e.g., a GPU), which is used for supporting a mobile TV, may be included in the electronic device 701. The processing device for supporting a mobile TV may process media data according to the standards of DMB, digital video broadcasting (DVB), MediaFlo®, or the like.

Each of the above-mentioned elements of the electronic device 701 according to various embodiments of the present disclosure may be configured with one or more components, and the names of the elements may be changed according to the type of the electronic device 701. The electronic device 701 according to various embodiments of the present disclosure may include at least one of the above-mentioned elements, and some elements may be omitted or other additional elements may be added. Furthermore, some of the elements of the electronic device 701 according to various embodiments of the present disclosure may be combined with each other so as to form one entity, so that the functions of the elements may be performed in the same manner as before the combination.

At least a part of the electronic devices 100/701 (e.g., modules or functions thereof) or a method (or operations) according to various embodiments of the present disclosure may be implemented, for example, by an instruction which is stored in a computer-readable storage media in the form of a program module.

A module or a program module according to various embodiments of the present disclosure may include at least one of the above elements, or a portion of the above elements may be omitted, or additional other elements may be further included. Operations performed by a module, a program module, or other elements according to various embodiments of the present disclosure may be executed sequentially, in parallel, repeatedly, or in a heuristic method. Also, a portion of operations may be executed in different sequences, omitted, or other operations may be added.

In accordance the embodiments described herein, when a user is using the exercise service module 110 of the electronic devices 100/701, while performing an exercise, the exercise history information may be continuously recorded, thereby providing a continuity of the exercise history information, such as in the case when the exercise service provided by the exercise service module 110 (or components associated therewith) is abnormally/unintentionally terminated.

While the present disclosure has been shown and described with reference to certain embodiments thereof, it will be understood by those skilled in the art that various changes in form and details may be made therein without departing from the scope of the present disclosure. Therefore, the scope of the present disclosure should not be defined as being limited to the embodiments, but should be defined by the appended claims and equivalents thereof.

What is claimed is:

1. An electronic device, comprising:
a display;
a processor configured to record exercise history information relating to an exercise performed by a user of the electronic device; and
a memory configured to store the exercise history information;
wherein the processor is configured to:
record the exercise history information continuously if an exercise application of the electronic device is unintentionally terminated,
retrieve the stored exercise history information when the exercise application is restarted, and
output at least one of a user interface on the display and audio information for notifying the user of an unintentional termination of the exercise application during the exercise.

2. The electronic device of claim 1, wherein the unintentional termination of the exercise application comprises at least one of where the exercise application is forcibly terminated due to insufficient memory, where the exercise application is forcibly terminated due to an error of the exercise application, where the exercise application is forcibly terminated by an application managing module, and where the user terminates the exercise application arbitrarily and forcibly.

3. The electronic device of claim 1, wherein the exercise history information comprises at least one of an exercise time, exercise information, real-time exercise data, and an exercise progress rate.

4. The electronic device of claim 1, wherein the processor is further configured to execute the exercise application in response to a selection of a display object of the user interface, and display a screen relating to the exercise application based on the exercise history information relating to the exercise.

5. The electronic device of claim 1, wherein the processor is further configured to display a screen of the exercise application based on the exercise history information relating to the exercise when the exercise application is first executed after the exercise application is unintentionally terminated.

6. The electronic device of claim 1, wherein the processor is further configured to display an object which guides to determine whether to restart the exercise when the exercise application is first executed after the exercise application is unintentionally terminated.

7. The electronic device of claim 6, wherein the processor is further configured to delete the exercise history information when the restart of the exercise is cancelled.

8. The electronic device of claim 6, wherein the processor is further configured to display a screen, which is the same as or similar to a screen displayed at a point in time when the exercise application is unintentionally terminated, based on the exercise history information, when the restart of the exercise is selected.

9. The electronic device of claim 8, wherein the processor is further configured to output at least one of a user interface on the display of the electronic device and audio information corresponding to information of the exercise based on the exercise history information, at a point in time of a termination of the exercise after the exercise restarts or at a point in time when the exercise history information is displayed after the exercise restarts.

10. A method for managing exercise history information in an electronic device, the method comprising:
    recording exercise history information relating to an exercise performed by a user of the electronic device continuously if an exercise application of the electronic device is unintentionally terminated;
    storing the exercise history information;
    retrieving the stored exercise history information when the exercise application is restarted; and
    outputting at least one of a user interface on a display of the electronic device and audio information for notifying the user of an unintentional termination of the exercise application during the exercise.

11. The method of claim 10, wherein the recording of the exercise history information comprises recording the exercise history information due to one of when the exercise application is forcibly terminated due to insufficient memory, when the exercise application is forcibly terminated due to an error of the exercise application, when the exercise application is forcibly terminated by an application managing module, and when the user terminates the exercise application arbitrarily and forcibly.

12. The method of claim 10, wherein the recording of the exercise history information comprises recording at least one of an exercise time, exercise information, real-time exercise data, and an exercise progress rate in the exercise history information.

13. The method of claim 10, further comprising:
    executing the exercise application in response to a selection of a display object of the user interface; and
    displaying a screen relating to the exercise application based on the exercise history information relating to the exercise.

14. The method of claim 10, further comprising displaying a screen of the exercise application based on the exercise history information relating to the exercise when the exercise application is first executed after the exercise application is unintentionally terminated.

15. The method of claim 10, further comprising displaying an object which guides to determine whether to restart the exercise when the exercise application is first executed after the exercise application is unintentionally terminated.

16. The method of claim 15, further comprising deleting the exercise history information when the restart of the exercise is cancelled.

17. The method of claim 15, further comprising displaying a screen, which is the same as or similar to a screen displayed at a point in time when the exercise application is unintentionally terminated, based on the exercise history information, when the restart of the exercise is selected.

18. The method of claim 17, further comprising outputting at least one of a user interface on the display of the electronic device and audio information corresponding to information of the exercise based on the exercise history information, at a point in time of a termination of the exercise after the exercise restarts or at a point in time when the exercise history information is displayed after the exercise restarts.

* * * * *